(12) United States Patent
Biedermann et al.

(10) Patent No.: US 9,387,093 B2
(45) Date of Patent: Jul. 12, 2016

(54) INTERVERTEBRAL IMPLANT

(71) Applicant: BIEDERMANN TECHNOLOGIES GMBH & CO. KG, Donaueschingen (DE)

(72) Inventors: Lutz Biedermann, VS-Villingen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 13/725,221

(22) Filed: Dec. 21, 2012

(65) Prior Publication Data
US 2013/0166030 A1    Jun. 27, 2013

Related U.S. Application Data

(60) Provisional application No. 61/579,522, filed on Dec. 22, 2011.

(30) Foreign Application Priority Data

Dec. 22, 2011 (EP) .................................. 11195380

(51) Int. Cl.
A61F 2/44 (2006.01)
A61F 2/46 (2006.01)
A61F 2/30 (2006.01)

(52) U.S. Cl.
CPC ............... *A61F 2/4611* (2013.01); *A61F 2/442* (2013.01); *A61F 2/3094* (2013.01);
(Continued)

(58) Field of Classification Search
CPC ........... A61F 2/44; A61F 2/441; A61F 2/442; A61F 2/4425; A61F 2002/443; A61F 2/4455; A61F 2002/4475

USPC .................... 623/17.11–17.16; 606/246–263
See application file for complete search history.

(56) References Cited

U.S. PATENT DOCUMENTS 5,554,191 A * 9/1996 Lahille et al. ............... 623/17.11
5,676,702 A * 10/1997 Ratron ........................ 623/17.16
(Continued)

FOREIGN PATENT DOCUMENTS

CN    101198298 A    6/2008
EP    1552797 A2    7/2005
(Continued)

OTHER PUBLICATIONS

Extended European Search Report and Opinion mailed May 21, 2012 for EPO Application No. EP 11195380.8, 7 sheets.

*Primary Examiner* — Pedro Philogene
*Assistant Examiner* — David C Comstock
(74) *Attorney, Agent, or Firm* — Lewis Roca Rothgerber Christie LLP (57) ABSTRACT

An intervertebral implant is provided comprising a single piece hollow body with an upper wall configured to engage a first vertebral end plate and a lower wall configured to engage a second vertebral end plate, with two opposite sidewalls connecting the upper wall and the lower wall, respectively, and with a load transmitting part configured to transmit load between the upper wall and the lower wall; wherein the body is configured to assume a compressed condition in which a distance between the upper wall and the lower wall defines a first height ($h_1$) of the implant and an expanded condition in which the distance between the upper wall and the lower wall defines a second height ($h_2$) of the implant that is greater than the first height ($h_1$); and wherein the implant is made of a material that exhibits shape memory properties.

20 Claims, 10 Drawing Sheets

(52) U.S. Cl.
CPC ............... *A61F 2002/30471* (2013.01); *A61F 2002/30484* (2013.01); *A61F 2002/30565* (2013.01); *A61F 2002/30579* (2013.01); *A61F 2002/30596* (2013.01); *A61F 2002/30598* (2013.01); *A61F 2002/30878* (2013.01); *A61F 2002/30879* (2013.01); *A61F 2002/4475* (2013.01); *A61F 2002/4623* (2013.01); *A61F 2002/4624* (2013.01); *A61F 2002/4627* (2013.01); *A61F 2210/0014* (2013.01); *A61F 2210/0019* (2013.01); *A61F 2310/00023* (2013.01)

(56) References Cited

U.S. PATENT DOCUMENTS

| | | | | |
|---|---|---|---|---|
| 6,143,031 | A * | 11/2000 | Knothe et al. | 623/17.16 |
| 7,625,377 | B2 * | 12/2009 | Veldhuizen et al. | 606/90 |
| 7,846,206 | B2 * | 12/2010 | Oglaza et al. | 623/17.11 |
| 7,993,403 | B2 * | 8/2011 | Foley et al. | 623/17.11 |
| 8,323,344 | B2 * | 12/2012 | Galley et al. | 623/17.16 |
| 8,540,452 | B2 * | 9/2013 | Jimenez et al. | 403/220 |
| 2001/0032020 | A1 | 10/2001 | Besselink | |
| 2003/0195631 | A1 | 10/2003 | Ferree | |
| 2006/0030943 | A1 * | 2/2006 | Peterman | 623/17.11 |
| 2006/0241757 | A1 * | 10/2006 | Anderson | 623/17.11 |
| 2006/0247771 | A1 * | 11/2006 | Peterman et al. | 623/17.11 |
| 2007/0219634 | A1 * | 9/2007 | Greenhalgh et al. | 623/17.16 |
| 2008/0167686 | A1 * | 7/2008 | Trieu et al. | 606/249 |
| 2008/0281346 | A1 * | 11/2008 | Greenhalgh et al. | 606/191 |
| 2009/0076613 | A1 | 3/2009 | Biedermann et al. | |
| 2009/0163918 | A1 | 6/2009 | Levy et al. | |
| 2009/0222100 | A1 * | 9/2009 | Cipoletti et al. | 623/17.16 |
| 2010/0131009 | A1 * | 5/2010 | Roebling et al. | 606/249 |
| 2013/0123927 | A1 * | 5/2013 | Malandain | 623/17.16 |

FOREIGN PATENT DOCUMENTS

| | | |
|---|---|---|
| WO | WO 98-14142 A1 | 4/1998 |
| WO | WO 01-01895 A1 | 1/2001 |
| WO | WO 2005-097006 A2 | 10/2005 |
| WO | WO 2006-116761 A2 | 11/2006 |
| WO | WO 2006/118853 A1 | 11/2006 |
| WO | WO 2007-009107 A2 | 1/2007 |
| WO | WO 2007-075878 A2 | 7/2007 |

* cited by examiner

INTERVERTEBRAL IMPLANT

CROSS-REFERENCE TO RELATED APPLICATION(S)

The present application claims the benefit of U.S. Provisional Patent Application Ser. No. 61/579,522, filed Dec. 22, 2011, the contents of which are hereby incorporated by reference in their entirety, and claims priority to European Patent Application EP 11 195 380.8, filed Dec. 22, 2011 the contents of which are hereby incorporated by reference in their entirety.

BACKGROUND

1. Field of the Invention

The invention relates to an intervertebral implant comprising a hollow body made in one piece and having an upper wall configured to engage a first vertebral end plate, a lower wall configured to engage a second vertebral end plate, two opposite sidewalls connecting the upper wall and the lower wall, respectively, and a load transmitting part configured to transmit load between the upper wall and the lower wall. The implant can assume a compressed condition in which it has a first height and a first width and an expanded condition in which it has a second height greater than the first height. The implant is made of a material that exhibits shape memory properties such that the implant can assume the expanded condition upon heating it.

2. Description of Related Art

US 2003/0195631 A1 describes spacers made of a shape-memory material that are used to ease insertion into an intradiscal space. The known spacer that is adapted to artificial disc replacement surgery comprises a piece of shape-memory material that is flattened or otherwise compacted prior to insertion and assumes a desired biconvex shape after it is positioned.

Other intervertebral disc prostheses using properties of shape-memory metals are known. For example, US 2009/0076613 A1 describes an intervertebral disc prosthesis including a base plate, a top plate, and at least two springs arranged between the base plate and the top plate, wherein the springs each have a loop-shaped section and two ends that are connected to the base plate and the top plate, respectively. The springs may be made of a shape-memory alloy.

SUMMARY

It is the object of embodiments of the invention to provide an intervertebral implant that can be used, for example, for intervertebral disc replacement, and that has a simple design with few parts and that provides for convenient handling.

The intervertebral implant is a one piece implant that has small dimensions in the compressed state and permits expansion in at least one spatial direction. In the expanded condition, it is configured to transmit loads from one vertebra to the other vertebra. The shape of the implant in the expanded condition may be pre-deformed such that the expanded condition may be achieved automatically when the implant is inserted and had assumed body temperature.

The small design of the implant in the compressed state facilitates the insertion of the intervertebral implant. The insertion may additionally be facilitated by the provision of rounded wall portions that are intended to be introduced first into the intervertebral space. In the compressed condition, the intervertebral end plates may be protected from being engaged with engagement portions on the implant which allows safe and convenient handling. In the expanded condition, the intervertebral implant is secured by engagement with the vertebral end plates.

BRIEF DESCRIPTION OF THE DRAWINGS

Further features and advantages of the invention will become apparent from the description of embodiments by means by the accompanying drawings. In the drawings:

FIGS. 22 to 27 show schematically steps of insertion of the intervertebral implant between two vertebrae;

FIG. 28a shows an anterior view of the intervertebral implant inserted into the intervertebral space in the expanded condition;

FIGS. 28b and 28c show enlarged views of details of FIG. 28a;

DETAILED DESCRIPTION

As shown in FIGS. 1 to 4, the intervertebral implant 10 according to a first embodiment is a one piece hollow body that comprises an upper wall 1, a lower wall 2 and side walls 3, 4 connecting the upper wall 1 and the lower wall 2. The length l of the upper wall 1 and the lower wall 2 is such that the intervertebral implant 10 can be accommodated fully in the intervertebral space between two vertebrae. The width $w_1$ of the upper wall 1 and the lower wall 2 is smaller than the length l. The thickness of the walls and the dimensions are such that the implant has substantially the shape of a closed loop made of a flat strip as shown, for example, in FIG. 2. In particular, the dimensions are such that the implant includes the ability to assume a compressed condition as shown in FIGS. 1 to 4 in which the distance between the upper wall 1 and the lower wall 2 is smallest and defines a first height $h_1$ of the implant 10 and an expanded condition shown in FIGS. 9 to 12 where the distance between the upper wall 1 and the lower wall 2 is greatest and defines a second height $h_2$ of the implant 10. The side walls 3, 4 are bent outward so that they have a rounded shape to facilitate insertion of the implant 10 into the intervertebral space.

Figure 2:
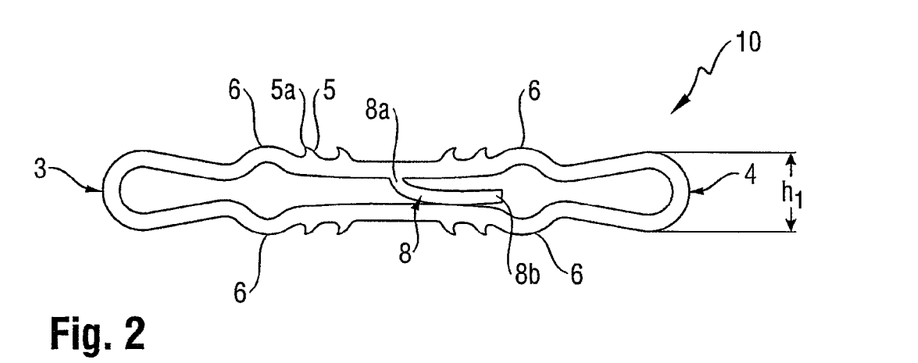
FIG. 2 shows a side view of the intervertebral implant of FIG. 1.

A plurality of engagement portions 5 are provided at the upper wall 1 and the lower wall 2. The engagement portions 5 are shaped as ribs 5 with substantially sharp free edges 5a that are bent outward in the direction of the side walls 3, 4. The ribs 5 extend across the full width of the intervertebral implant 10. In the embodiment shown, the ribs 5 are arranged in groups offset from the center and along the length of the intervertebral implant 10. Between the side walls 3, 4 and the ribs 5, bulges 6 are provided in the upper wall 1 and the lower wall 2 that extend across the width of the walls 1, 2. In the compressed condition, as best shown in FIG. 2, the bulges 6 have such a height in relation to the engagement portions 5 that the bulges 6 prevent engagement of the engagement portions 5 with the end plates of the vertebrae during the insertion procedure.

Figure 3:
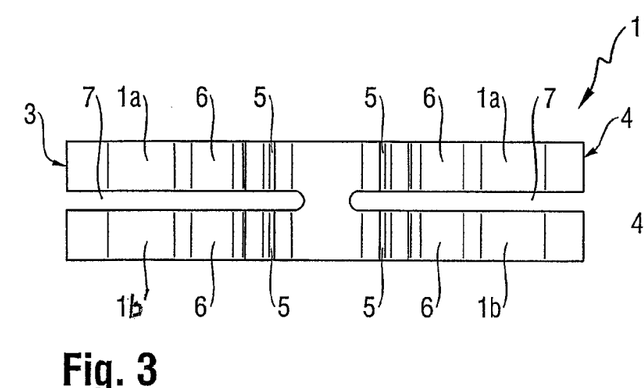
FIG. 3 shows a top view of the intervertebral implant of FIG. 1.
Figure 4:
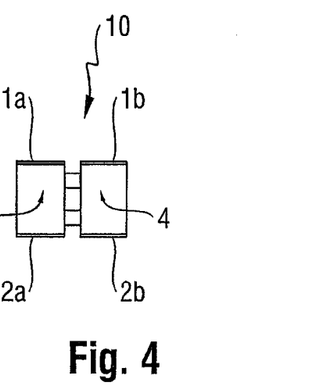
FIG. 4 shows another side view of the intervertebral implant of FIG. 1.
Figure 5:
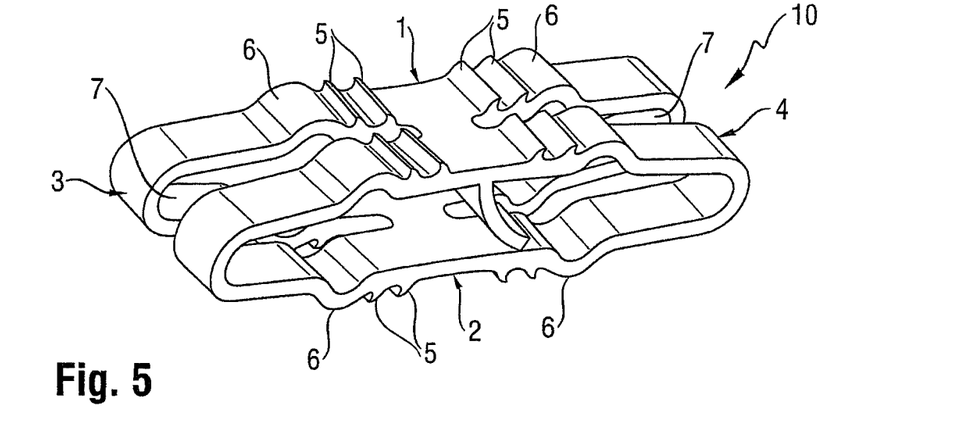
FIG. 5 shows a perspective view of the intervertebral implant according to the first embodiment in an intermediate condition.
Figure 6:
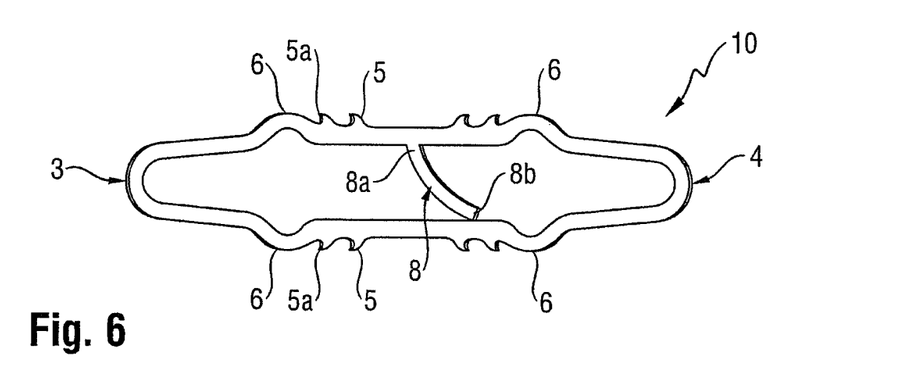
FIG. 6 shows a side view of the intervertebral implant of FIG. 5.
Figure 7:
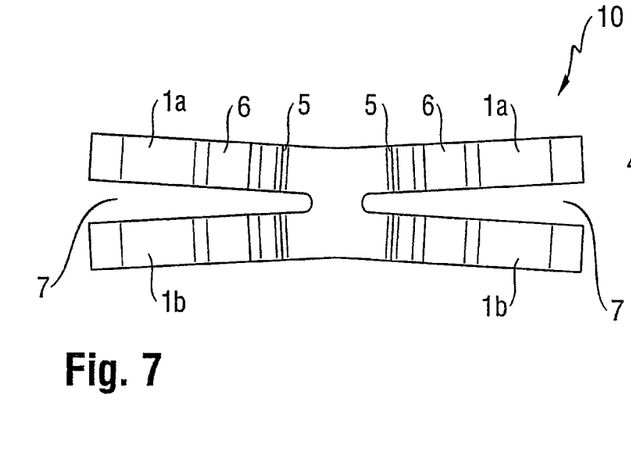
FIG. 7 shows a top view of the intervertebral implant of FIG. 5.
Figure 8:
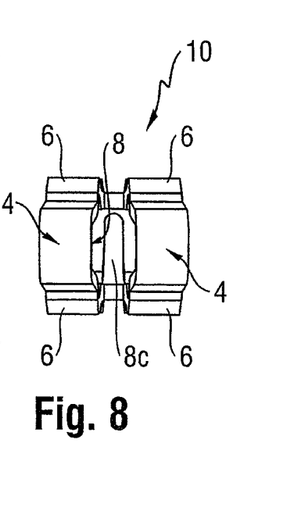
FIG. 8 shows another side view of the intervertebral implant of FIG. 5.

The intervertebral implant 10 further comprises two opposite slits 7 that extend in a length-wise direction through the side walls 3, 4 and through the upper and lower walls 1, 2 until a distance from the center of the implant 10. The length of each slit 7 is greater than the distance between the slits 7 as seen in FIG. 3. Hence, from the top view, as seen in FIG. 3, the intervertebral implant 10 looks substantially H-shaped. As a result of the slits 7, the implant 10 is bifurcated and forms first and second upper wall portions 1a, 1b and first and second lower wall portions 2a, 2b as shown in FIGS. 3 and 4.

Figure 1:
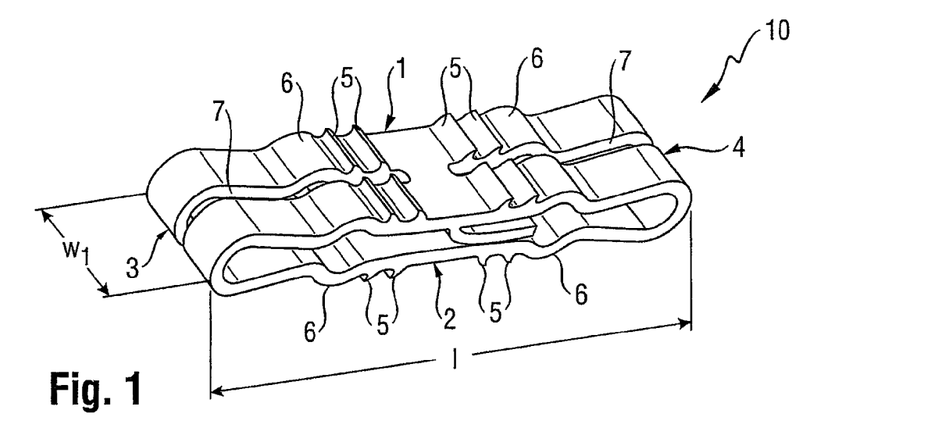
FIG. 1 shows a perspective view of a first embodiment of the intervertebral implant in the compressed condition.
Figure 9:
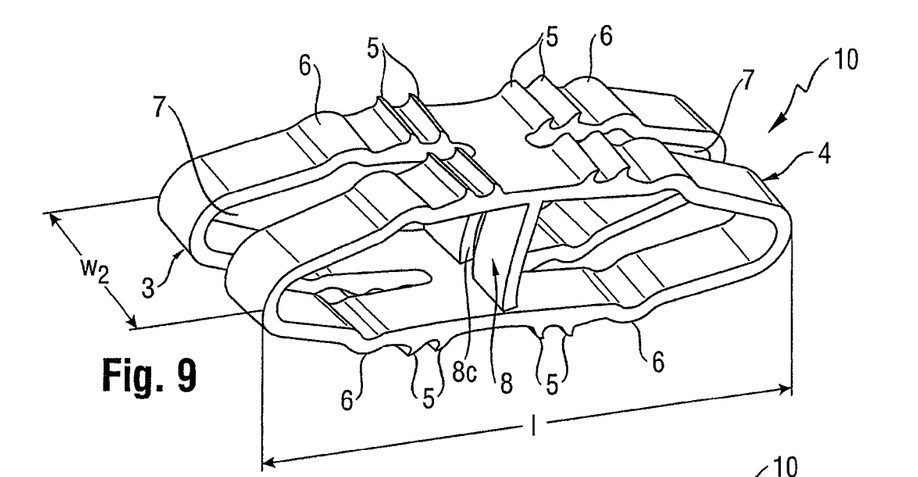
FIG. 9 shows a perspective view of the intervertebral implant according to the first embodiment in the expanded condition.
Figure 10:
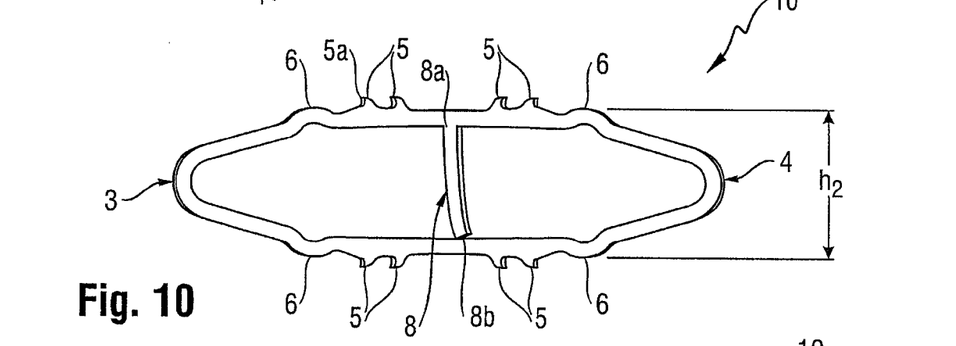
FIG. 10 shows a side view of the intervertebral implant of FIG. 9.
Figure 11:
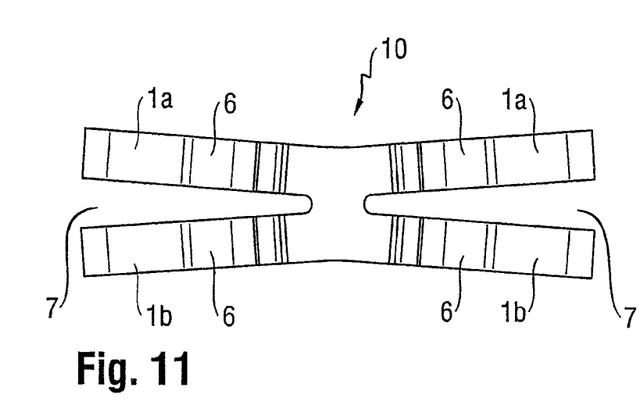
FIG. 11 shows a top view of the intervertebral implant of FIG. 9.
Figure 12:
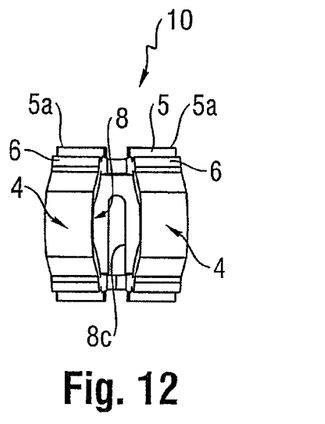
FIG. 12 shows another side view of the intervertebral implant of FIG. 9.
Figure 13:
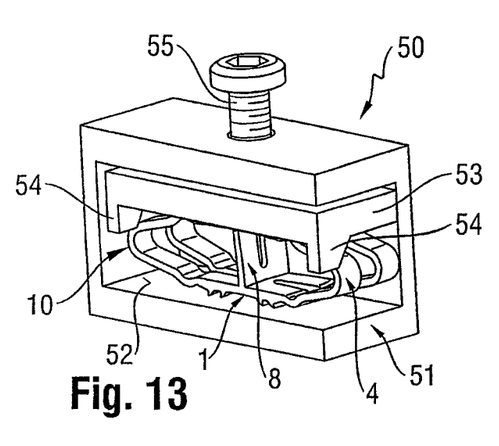
FIG. 13 shows a perspective view of a device for compressing the intervertebral implant with an intervertebral implant inserted therein in the expanded condition.
Figure 14:
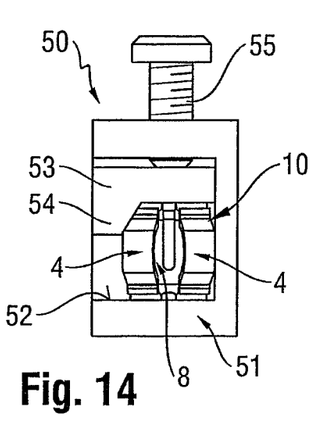
FIG. 14 shows a side view of the device with implant according to FIG. 13.
Figure 15:
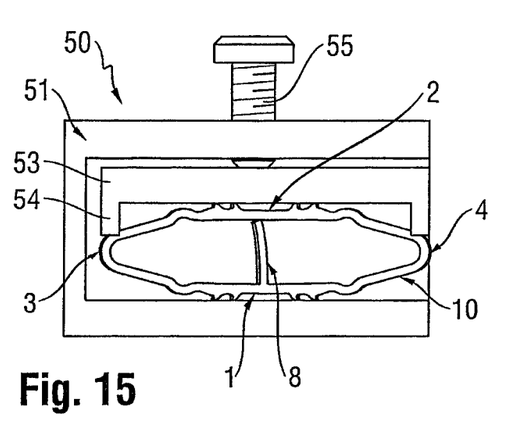
FIG. 15 shows another side view of the device with implant of FIG. 13.
Figure 16:
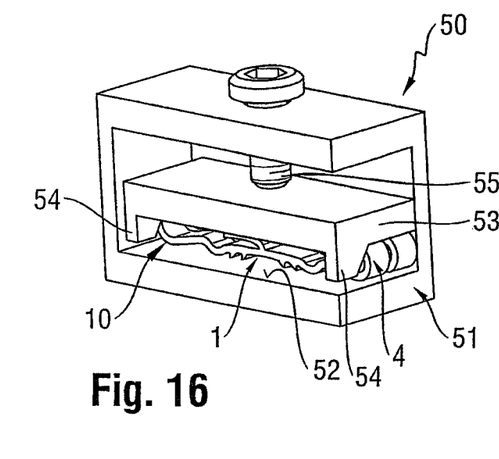
FIG. 16 shows a perspective view of the device for compressing the intervertebral implant with inserted and compressed intervertebral implant.
Figure 17:
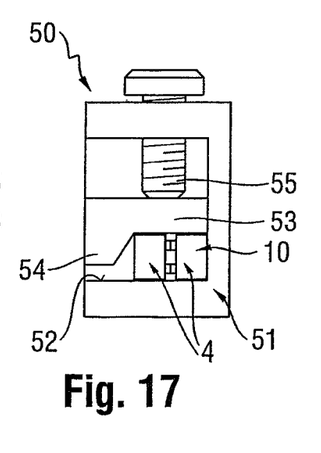
FIG. 17 shows a side view of the device with implant of FIG. 16.
Figure 18:
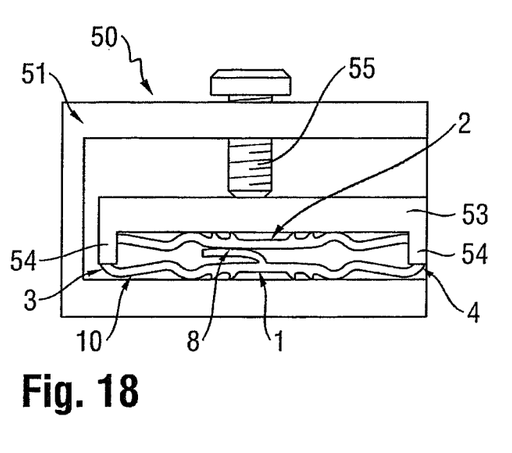
FIG. 18 shows another side view of the device with implant of FIG. 16.

At the center of the implant's length a strut 8 is provided that has a first end 8a and a second end 8b. The first end 8a is formed in one piece with the upper wall 1. The second end 8b is free. The strut 8 has a thickness that allows it to be deformable. As shown in FIGS. 1 and 2, the strut 8 is deformable in such a way that in the compressed condition of the implant 10 a portion of the strut 8 between the first end 8a and the second end 8b contacts the lower wall 2 and said condition defines a minimum height $h_1$ of the upper wall 1 from the lower wall 2. Referring to FIGS. 9 and 10, in the expanded condition, the strut 8 extends substantially vertically or at a small angle with respect to the height direction of the implant 10. When the implant 10 is in the expanded condition, the free end 8b of the strut 8 is supported by the lower wall 2. A catch or locking ratcheting portion 20 may be provided for the strut 8 at the inside of the lower wall 2, as shown, for example, in FIG. 28c. Such a catch 20 may be, for example, a shallow indentation or a recess that catches the free end 8b of the strut 8. Furthermore, a slit 8c in the strut 8 extends from the free end 8b towards the first end 8a such that the strut 8 is also bifurcated, as can be best seen in FIGS. 9 and 12.

The intervertebral implant 10 is configured to assume two end conditions—the compressed condition in which the distance between the upper wall 1 and the lower wall 2 in the height direction is smallest as shown in FIGS. 1 to 4 and the expanded condition as shown in FIGS. 9 to 12 in which the distance between the upper wall 1 and lower wall 2 is greatest—and intermediate conditions therebetween. FIGS. 5 to 8 show an intermediate condition, in which the distance between the upper wall 1 and the lower wall 2 is not yet the full distance in the height direction.

Referring to FIGS. 5 to 12, from the intermediate to the expanded conditions, the distance between the upper wall 1 and the lower wall 2 increases so that the height of the implant 10 increases. Also, the slits 7 expand to assume a V-shape with increasing width towards the side walls 3, 4. This results in the upper wall portions 1a, 1b and the lower wall portions 2a, 2b, respectively, having an increased distance from each other as the distance from the center of the implant 10 increases. Hence, as shown best in FIG. 12, the intervertebral implant 10 has a slight X-shape in a top view. Therefore, the width of the implant 10 in the intermediate and expanded conditions is increased compared to the compressed condition. Thus, the intervertebral implant 10 is configured to expand three-dimensionally in two spatial directions.

In the expanded condition, as shown in the side view of FIG. 10, the portions of the upper and lower walls 1, 2 adjacent the side walls 3, 4 comprise a substantially V-shaped cross-section. In the center part of the implant 10, the upper wall 1 and the lower wall 2 are at the greatest distance from each other. The bulges 6 no longer project above the engagement portions 5. Therefore, the engagement portions 5 project out of the upper and lower walls 1, 2 and are capable of engaging the end plates of the vertebrae.

The intervertebral implant 10 is made of a shape-memory material. Such a shape-memory material can be, for example, a shape-memory alloy, such as certain nickel-titanium alloys that exhibit shape-memory properties, in particular Nitinol. Also, the material can be a shape-memory polymer material.

The shape-memory property of shape-memory material results from a phase transition within the material at a transition temperature. The intervertebral implant 10 can be manufactured such that it assumes the pre-deformed expanded condition, as shown in FIGS. 9 to 12, at approximately body temperature or at a predefined temperature below body temperature. Then, the implant 10 is cooled down and compressed to assume the compressed condition. The compression can be performed, for example, with a device shown in FIGS. 13 to 18. The device 50 for compressing the implant 10 comprises a holder 51 that accommodates the implant 10 and comprises a support surface 52 for supporting, for example, the upper wall 1 of the implant 10. A press plate 53 is provided that is configured to be pressed against the opposite wall, in the example shown, the lower wall 2 of the implant 10. The press plate comprises projections 54 extending towards the support surface 52 at either end of the press plate. The projections 54 serve as lateral limiters that prevent further expansion of the implant 10 in width direction during compression of the implant's height. An actuator for moving the press plate 53 downward is further provided.

The compression of the implant can be made under cooling conditions to cool the implant 10 below the transition temperature. The implant 10 remains in the compressed condition unless it is heated above the transition temperature.

Figures 19, 20:
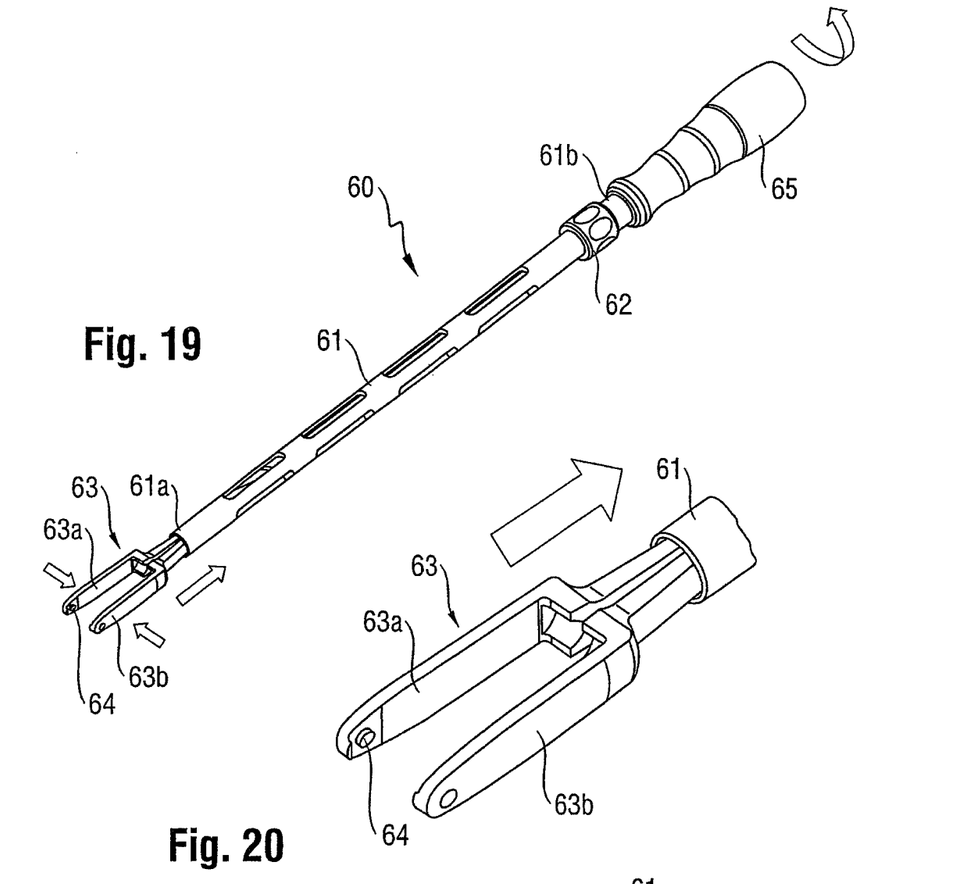
FIG. 19 shows a perspective view of a first embodiment of the device for insertion of the intervertebral implant.
FIG. 20 shows an enlarged portion of FIG. 19 with the device in a first condition.
Figure 21:
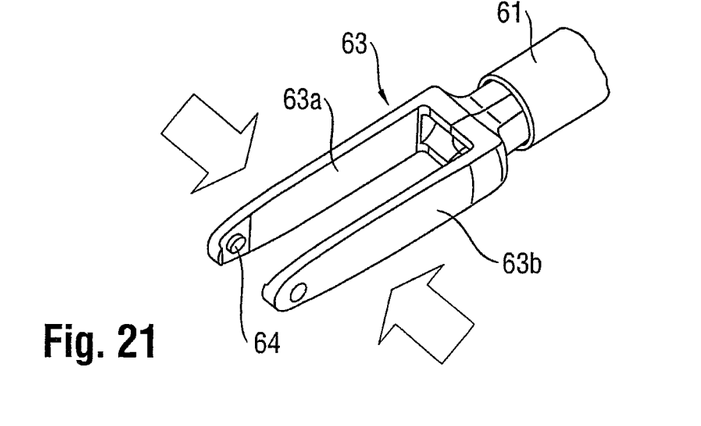
FIG. 21 shows an enlarged portion of FIG. 19 with the device in a second condition.
Figure 23:
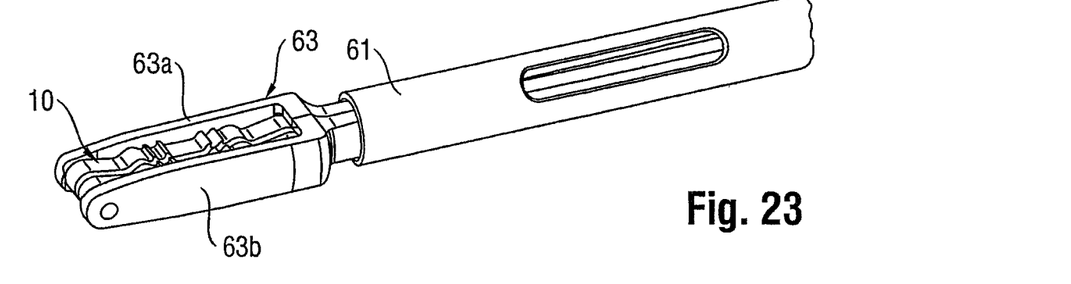

In FIGS. 19 to 21, the first embodiment of a tool for insertion of the intervertebral implant 10 is described. The tool 60 comprises a sleeve 61 having a first end 61a and an opposite second end 61b. A grip portion 62 may be provided on the sleeve, for example, near the second end 61b. Within the sleeve an actuating portion (not shown) for a gripper 63 is provided. The gripper 63 extends out of the sleeve at the first end 61a. The gripper 63 is fork-shaped and has two arms 63a, 63b that can assume an open condition, shown in FIG. 20, in which the arms 63a, 63b have a distance from each other greater than the width of the implant 10 and a closed condition, shown in FIG. 21, in which the arms 63a, 63b have a smaller distance from each other and wherein pins 64 at the ends of the arms 63a, 63b, that are directed to the inside of the fork, can engage the implant 10. A handle 65 may be provided that is connected to the actuator. Rotation of the handle in one direction draws the gripper 63 into the sleeve 61, as shown in FIG. 20, so that the arms 63a, 63b are closed as shown in FIG. 21. The length of the arms corresponds substantially to the length of the implant 10 in the compressed state, so that, as shown in FIG. 23, when the implant 10 is engaged by the pins 64 at one side wall 3, the other side wall 4 abuts against the end of the arms 63a, 63b.

Figure 22:
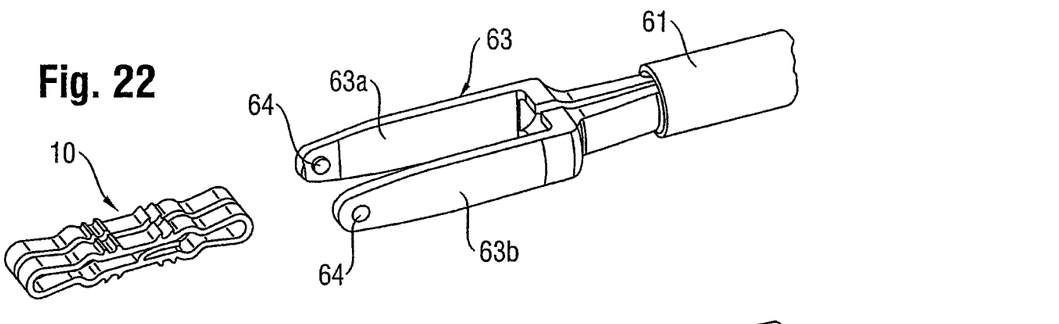

Use of the intervertebral implant 10 will be explained with reference to FIGS. 22 to 29. As shown in FIG. 22, the intervertebral implant 10 is in the compressed state prior to taking it up with the device for insertion 60. As shown in FIG. 23, the implant 10 is gripped between the arms 63a, 63b of the gripper 63 such that the pins 64 engage one side of the implant 10 and the opposite side is abutting against the bottom of the fork-shaped gripper 63. Hence, the intervertebral implant 10 is firmly held with the gripper 63.

Figure 24:
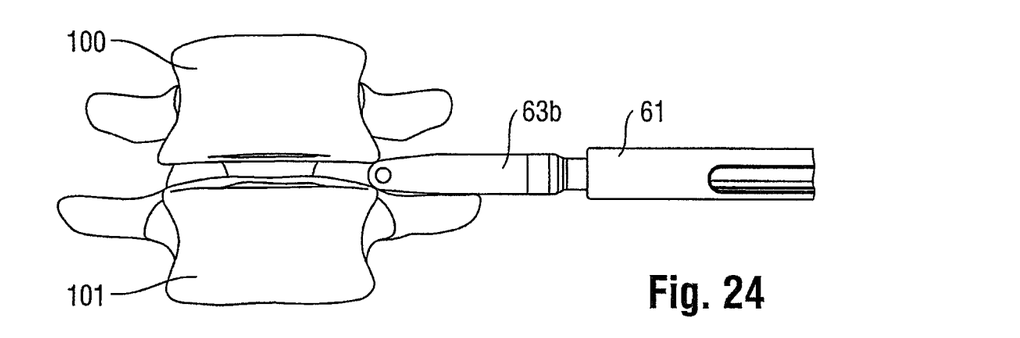
Figure 25:
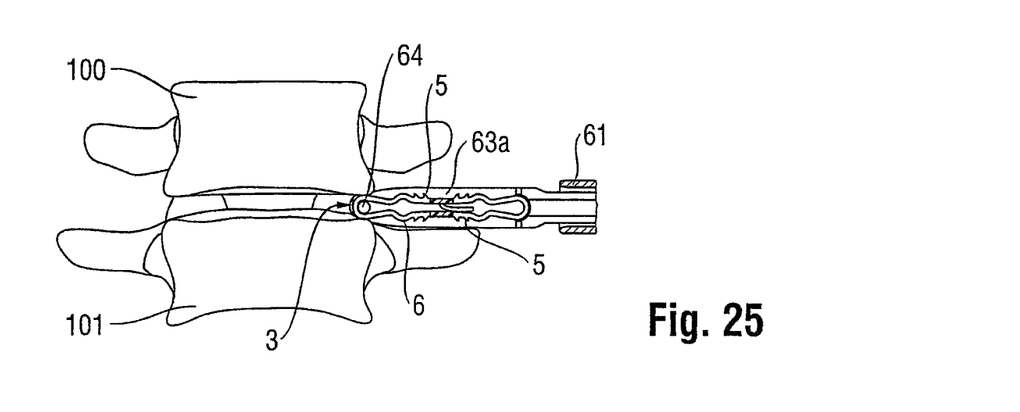
Figures 26, 27, 28A, 28C:
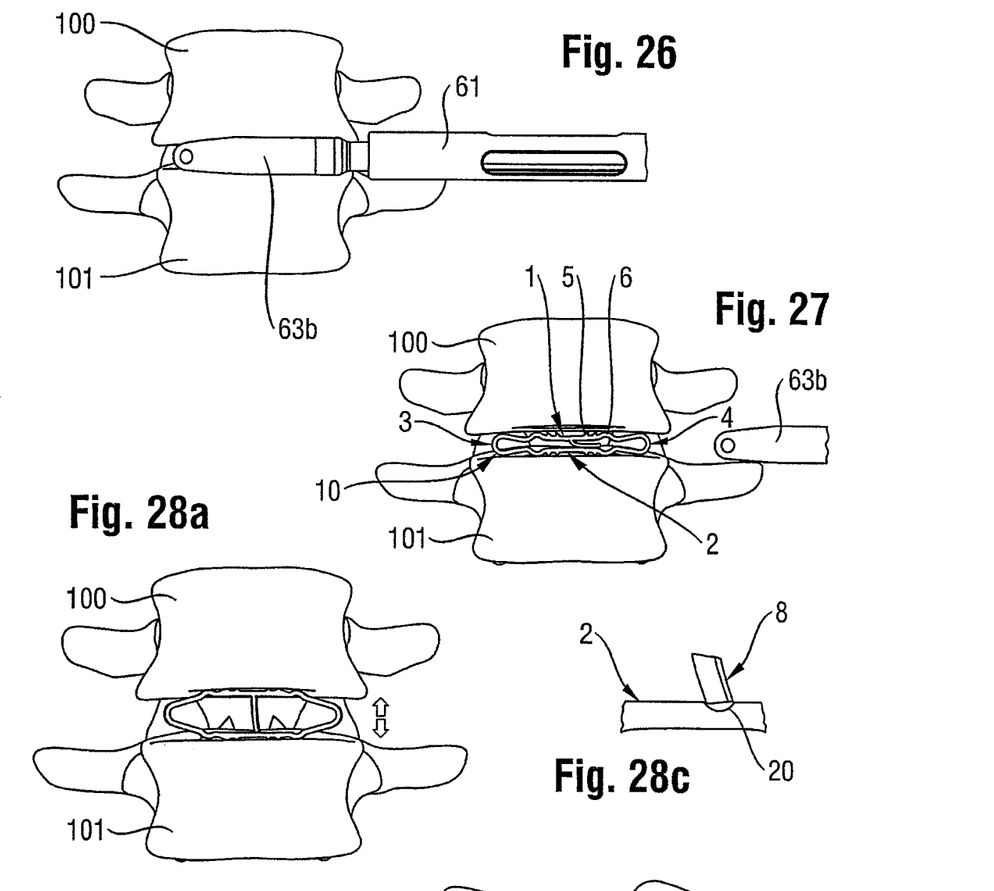
Figure 28B:
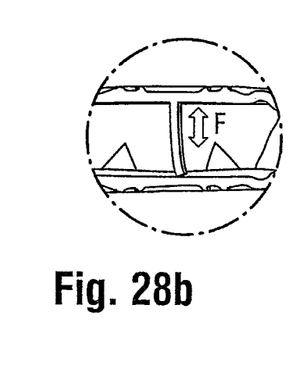
Figure 29:
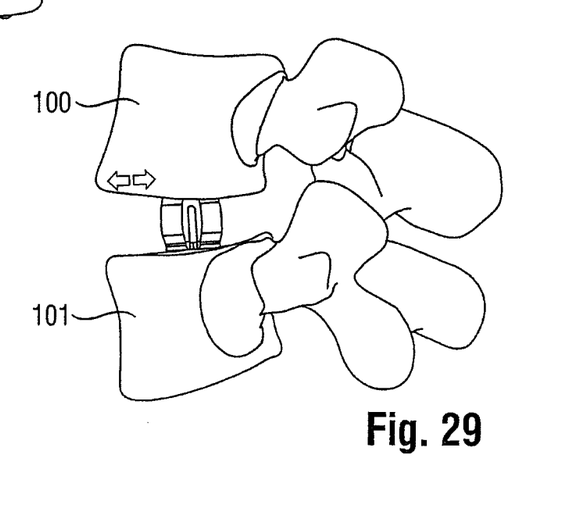
FIG. 29 shows a lateral view of the intervertebral implant inserted into the intervertebral space in the expanded condition.
Figure 30:
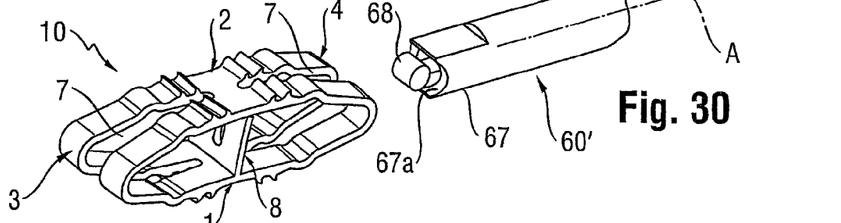
FIGS. 30 to 32 show a perspective view, a side view and a top view, respectively, of the intervertebral implant in the expanded condition with a second embodiment of the device for insertion.
Figure 31:
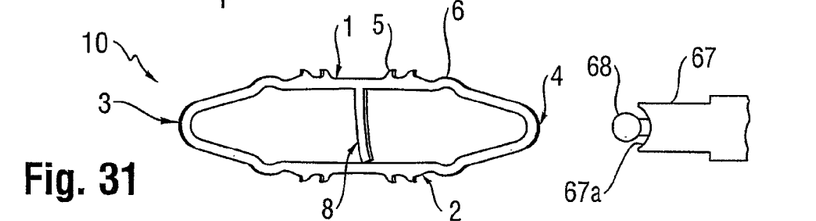

Then, the intervertebral implant 10 is introduced into the intervertebral space using a lateral approach as seen in FIGS. 24 to 26. As shown in FIG. 24, the rounded edges of the arms 63a, 63b and the rounded side walls 3, 4 serve for smoothly inserting the implant 10. As can be seen in FIG. 25, the bulges 6 in the compressed condition of the implant 10 have the same height or are slightly higher than the crests 5a of the engagement portions 5 so that during insertion the rounded shape of the bulges 6 protects the vertebral end plates from being injured by the engagement portions 5. In the finally inserted state as shown in FIG. 26, the implant 10 held by the arms 63a, 63b of the gripper 63 has been fully introduced. Then, the arms 63a, 63b of the gripper 63 are opened and the device for insertion 60 is carefully removed. As best seen in FIG. 27, the implant 10 is still in the compressed condition. By the action of the body heat, the implant 10 begins to expand as shown in FIG. 28a, thereby enlarging the intervertebral space. In the expanded condition, the engagement portions 5 engage the vertebral end plate to prevent movement of the intervertebral implant 10. The strut 8 finally extends substantially vertically and maybe caught in the catch 20 as shown in FIGS. 28b and 28c. In the expanded condition, the strut 8 additionally bears the load that acts onto the upper wall 1 and transmits it to the lower wall 2. During expansion, the intervertebral implant 10 also expands in the width direction, as shown in FIG. 29, thereby permitting a load transfer over a greater width which renders the implant 10 more stable.

Figure 32:
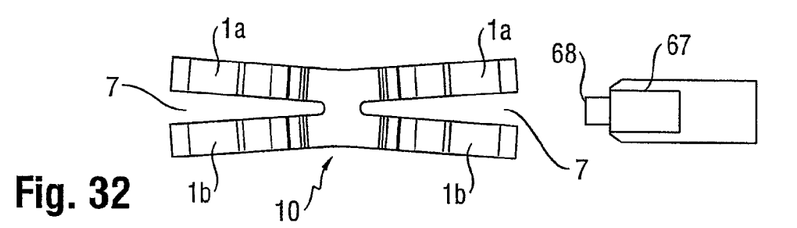
Figure 33:
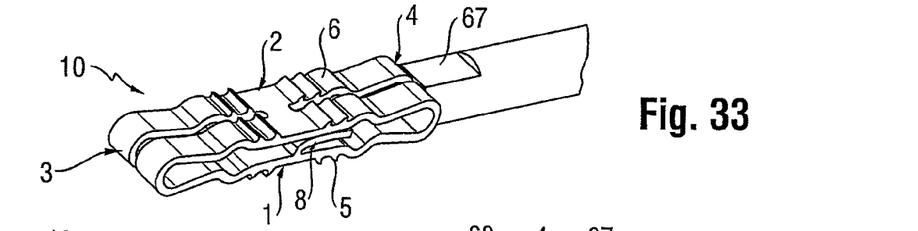
FIGS. 33 to 35 show a perspective view, a side view and a top view, respectively, of the intervertebral implant in the compressed condition with the second embodiment of the device for insertion attached thereto.
Figure 34:
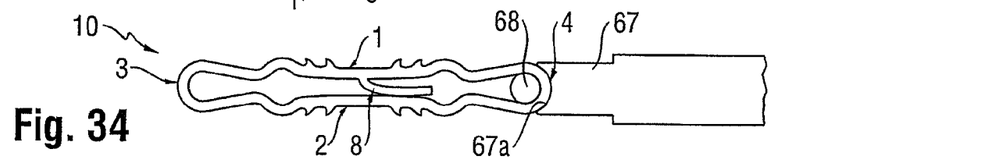
Figure 35:
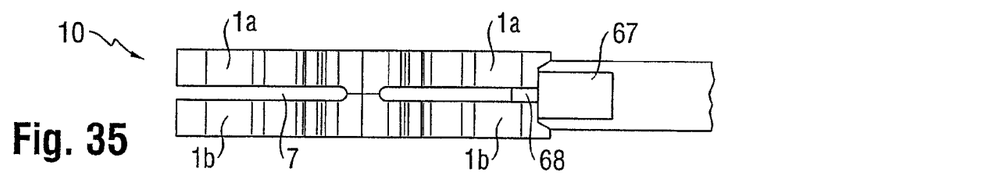

Referring to FIGS. 30 to 35, a second embodiment of the device for insertion is shown. The device for insertion 60' comprises a gripper 67 that has a front portion 67a from which a pin 68 extends at a distance to the front portion 67a in a direction perpendicular to a longitudinal axis A of the gripper 67. The length of the pin 68 is smaller than the width of the slits 7 when the implant 10 is in the expanded condition, as shown in FIG. 32, such that the pin 68 can be introduced into the implant 10 and removed therefrom in the expanded condition of the implant 10. The distance between the outer surface of the pin 68 and the rounded front portion 67a of the gripper 67 corresponds substantially to the thickness of the side wall 3, 4 such that, when the pin engages the implant 10 when the implant 10 is in the compressed condition as shown, for example in FIGS. 33-35, the gripper 67 can firmly hold the implant 10.

In use, the device for insertion 60' is coupled to the implant 10 in the expanded condition. Then, the implant 10 is compressed with the device for insertion 60 attached thereto. In the compressed condition, the gripper 67 and the implant 10 are connected to each other. Then, the implant 10 is inserted into the intervertebral space. After expansion of the implant 10, the gripper 67 can be removed since the length of the pin 68 will be shorter than the width of the slits 7.

Referring to FIGS. 36 to 41, a second embodiment of the intervertebral implant 10 and a third embodiment of the device of insertion will be explained.

Figure 36:
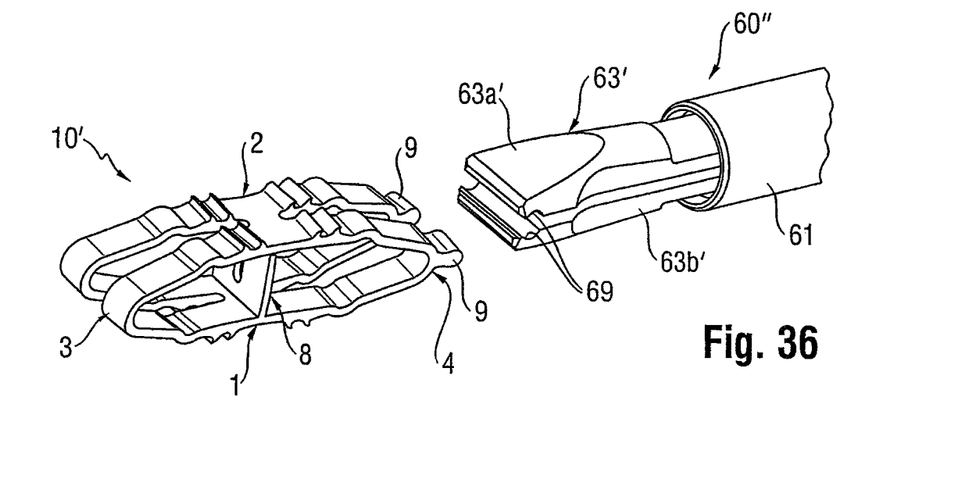
FIGS. 36 to 38 show a perspective view, a side view and a top view, respectively, of an intervertebral implant according to a second embodiment in the expanded condition with a device for insertion according to the third embodiment.
Figure 37:
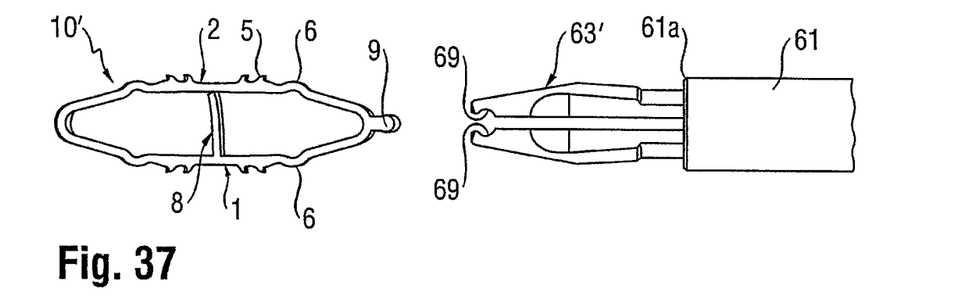
Figure 38:
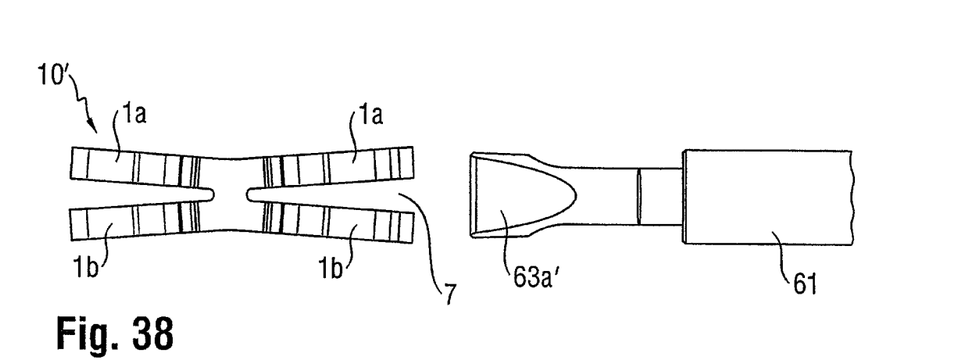

The intervertebral implant 10' according to the second embodiment has additionally at one side wall 3 a rib-shaped projection 9 extending laterally away from the side wall 4. Due to the slit 7, each upper wall portion 1a, 1b and each lower wall portion 2a, 2b are associated with the lateral projection 9. The outer end of the projection 9 has a substantially circular cross section.

Figure 39:
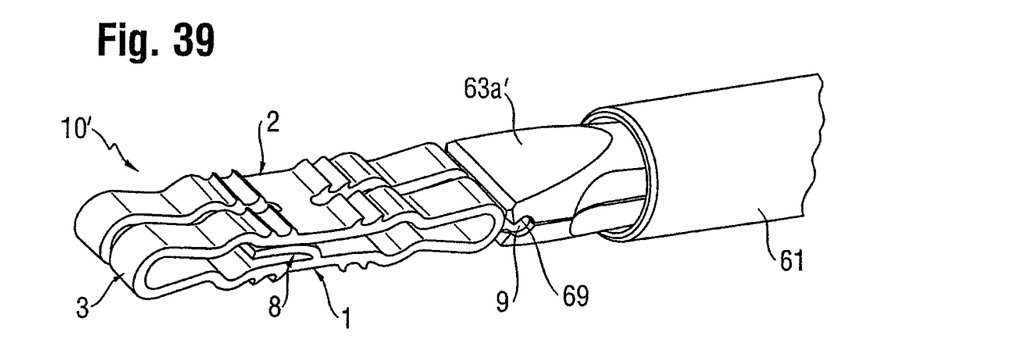
FIGS. 39 to 41 show a perspective view, a side view and a top view, respectively, of the intervertebral implant according to the second embodiment in the compressed condition with the device for insertion according to the third embodiment attached thereto
Figure 40:
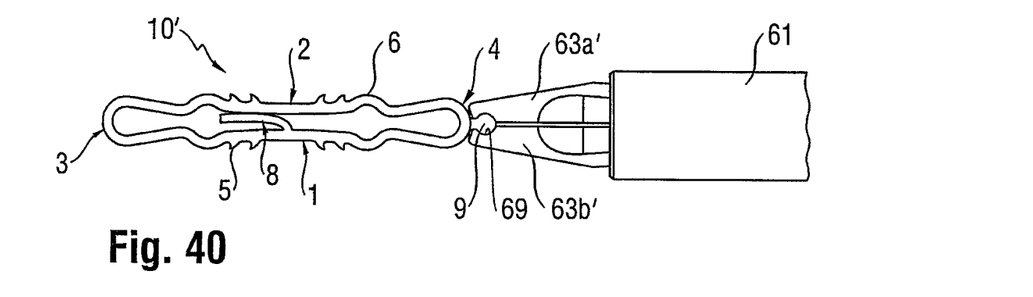
Figure 41:
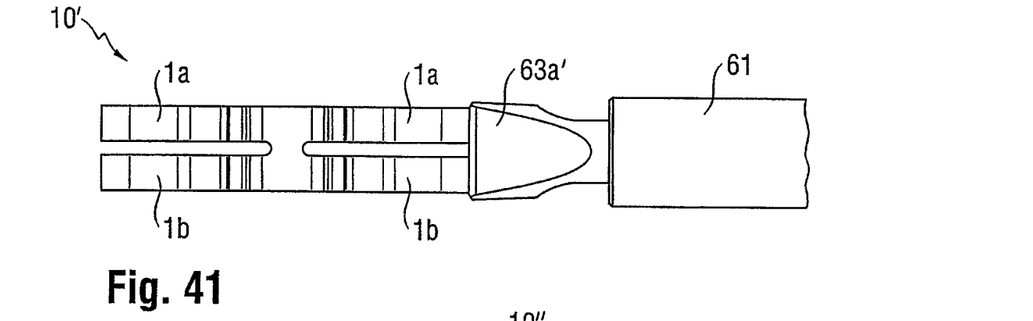

The device for insertion 60" according to the third embodiment is similar to the device for insertion 60 according to the first embodiment in that it comprises a sleeve 61 and a gripper 63' extending out from the first end 61a of the sleeve 61. The gripper 63' comprises arms 63a', 63b' that have cylindrical recesses 69 at a distance from their free end that match the shape of the lateral projections 9 of the implant 10'. The gripper 63' can assume an open position in which the arms 63a', 63b' have a distance from each other and that permits introduction of the lateral projection 9 of the implant 10'. The gripper 63' can then assume a closed position as shown in FIGS. 39 to 41, in which the lateral projection 9 is gripped by the arms 63a', 63b' and firmly held in the recesses 69. The width of the gripper 63' is such that substantially the whole lateral projection 9 in a width direction is accommodated between the arms 63a', 63b' of the gripper 63' when the implant 10' is in the compressed state, as shown in FIG. 39. The use of the implant 10' and a device for insertion 60" is similar of the use of the implant 10 and the device 60 in the first embodiment. The implant 10' is taken by the device for insertion 60" when it is in the compressed state. When the implant 10' is introduced between two vertebrae, the opposite side wall 4 that has no lateral projection 9 is the first portion to be introduced. Due to the rounded side wall 4, the introduction can be carried out gently.

Figure 42:
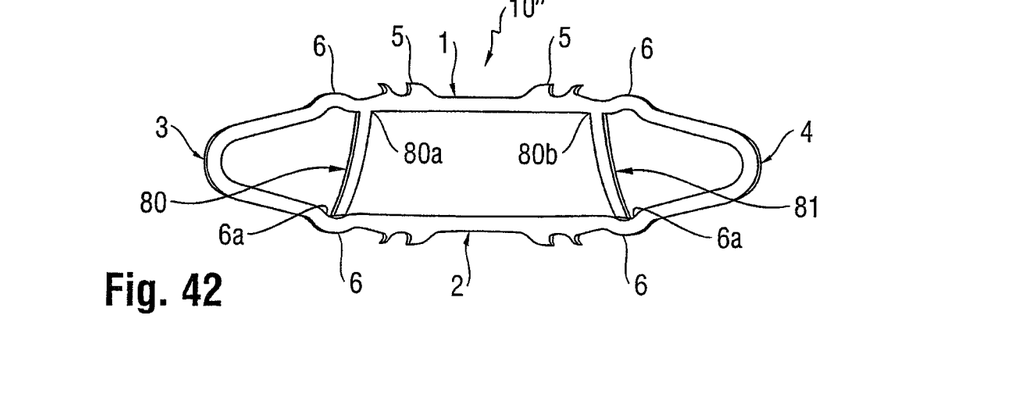
FIG. 42 shows a side view of a third embodiment of the intervertebral implant.

A third embodiment of the intervertebral implant is shown in FIG. 42. The implant 10" differs from the implants of the previous embodiments in that it comprises two struts 80, 81. The struts 80, 81 each have a first end 80*a*, 80*b*, integrally formed with the upper wall 1 at a position between the projections 5 and the bulges 6. The second ends 80*b*, 81*b* of the struts 80, 81 are free and rests in a depression 6*a* at the inside of the lower wall 2 that corresponds to the bulges 6 when the implant 10" is in the expanded condition. In the compressed condition, the struts 80, 81 are deformed towards the side walls 3, 4. The struts 80, 81 also have slits (not shown). The other portions of the implant 10" are the same as in the first or second embodiment.

Modifications of the above described embodiments are conceivable. More than two struts may be provided. The struts may have another shape that permits the transmission of loads. The struts may be integrally formed with the upper or with the lower wall. More than two slits 7 may be provided, hence giving the implant a more complex structure. For example, additional slits may be provided that allow an additional expansion. It is also conceivable that no slits are provided. In this case the expansion of the implant takes place only in one direction, for example, in the height direction.

The widths of the upper and lower walls need not be constant over their length. For example, the width may be greater at one end as compared to the other end.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. Intervertebral implant comprising:
  a monolithic body with an upper wall configured to engage a first vertebral end plate, a lower wall configured to engage a second vertebral end plate, and two opposite sidewalls each connecting the upper wall to the lower wall; and
  a strut configured to transmit load between the upper wall and the lower wall, the strut having a first end formed monolithically with a wall, the wall being either the upper wall or the lower wall, and a second end that is free;
  wherein at least a portion of the body between the two sidewalls is configured to assume a compressed condition in which a distance between the upper wall and the lower wall defines a first height of the implant and to assume an expanded condition in which the distance between the upper wall and the lower wall defines a second height of the implant that is greater than the first height;
  wherein the implant is made of a material that exhibits shape memory properties that cause the implant to change from the compressed condition to the expanded condition under predetermined conditions; and
  wherein, in the compressed condition, a portion of the strut extends at an angle to the wall with which the strut is monolithically formed, and in the expanded condition, the portion of the strut extends at a different angle to the wall with which the strut is monolithically.

2. The intervertebral implant of claim 1, wherein in the compressed condition, the portion of the strut extends substantially parallel to the upper wall or the lower wall and in the expanded condition, the portion of the strut extends substantially perpendicular to the upper wall or the lower wall.

3. The intervertebral implant of claim 1, wherein in the expanded condition, the portion of the strut extends substantially perpendicular to the upper wall or the lower wall.

4. The intervertebral implant of claim 1, wherein the second end of the strut is caught in a catch in the expanded condition.

5. The intervertebral implant of claim 1, wherein the strut extends across substantially an entire width of the upper wall or the lower wall.

6. The intervertebral implant of claim 1, wherein a shape of the implant in the expanded condition is pre-formed and wherein the shape of the implant in the compressed condition is achieved by deforming the pre-formed implant at a temperature below a transition temperature of the material.

7. The intervertebral implant of claim 1, wherein the two sidewalls, the upper wall and the lower wall form a closed monolithic loop and wherein a width from one open side of the closed monolithic loop to an opposite open side of the closed monolithic loop of the upper wall or the lower wall in the compressed condition defines a first width of the implant and wherein a width from the one open side of the closed monolithic loop to the opposite open side of the closed monolithic loop of the upper wall or the lower wall in the expanded condition defines a second width of the implant, the second width being greater than the first width.

8. The intervertebral implant of claim 1, wherein at least one slit is provided extending completely through at least one sidewall into the upper wall and the lower wall and wherein a width of the slit is substantially the same in the compressed condition and increases towards the at least one sidewall in the expanded condition.

9. The intervertebral implant of claim 8, wherein two slits are provided that extend from the sidewalls towards the center of the upper wall and the lower wall and wherein a length of the slits is larger than a greatest width of the slits.

10. The intervertebral implant of claim 1, wherein at least one of the sidewalls is rounded towards the outside.

11. The intervertebral implant of claim 1, wherein the upper wall and the lower wall comprise projections configured to engage the first and the second vertebral end plates and wherein the upper wall and the lower wall comprise bulges rounded towards the outside that are arranged between the sidewalls and the projections, the bulges projecting farther out than or being at equal height to the projections in the compressed condition.

12. The intervertebral implant of claim 1, further comprising a projection extending laterally from at least one of the sidewalls for engagement with an insertion device.

13. The intervertebral implant of claim 1, wherein, when viewed from the upper wall or the lower wall, the implant has a substantially H-shaped contour in the compressed condition and a substantially X-shaped contour in the expanded condition.

14. The intervertebral implant of claim 1, wherein at least one slit is provided extending completely through at least one sidewall into the upper wall and the lower wall and wherein a width of the slit at the sidewall in the compressed condition defines a first width of the slit and a width of the slit at the sidewall in the expanded condition defines a second width of the slit that is greater than the first width.

15. The intervertebral implant of claim 1, wherein the angle in the compressed condition is less than the different angle in the expanded condition.

16. The intervertebral implant of claim 1, wherein the upper wall and the lower wall comprise bone engaging surfaces configured to engage the first and the second vertebral end plates and wherein the upper wall and the lower wall comprise bulges rounded towards the outside of the monolithic body, wherein a distance between the upper and the lower wall at the bulges is greater than or equal to a distance between the upper and the lower wall at the bone engaging surfaces when in the compressed condition, and the distance between the upper and the lower wall at the bulges is less than the distance between the upper and the lower wall at the bone engaging surfaces when in the expanded condition.

17. The intervertebral implant of claim 1, wherein the upper wall and the lower wall comprise a central region bordered by bone engaging surfaces, wherein at least one slit is provided extending completely through at least one sidewall into the upper wall and the lower wall, the at least one slit extending into the central region.

18. The intervertebral implant of claim 1, wherein the two sidewalls, the upper wall and the lower wall form a closed loop that defines a width of the implant from one open side of the closed loop to the other open side and the width of the closed loop is less than the length of the implant between the two sidewalls.

19. Intervertebral implant comprising:
a monolithic body with an upper wall configured to engage a first vertebral end plate, a lower wall configured to engage a second vertebral end plate, and two opposite sidewalls each connecting the upper wall to the lower wall, wherein the two sidewalls, the upper wall and the lower wall form a closed loop; and
a strut configured to transmit load between the upper wall and the lower wall, the strut having a first end formed monolithically with a wall, the wall being either the upper wall or the lower wall, and a second end that is free;
wherein at least a portion of the body is configured to assume a compressed condition in which a distance between the upper wall and the lower wall defines a first height of the implant and to assume an expanded condition in which the distance between the upper wall and the lower wall defines a second height of the implant that is greater than the first height;
wherein the implant is made of a material that exhibits shape memory properties that cause the implant to change from the compressed condition to the expanded condition under predetermined conditions;
wherein in the compressed condition, a portion of the strut extends at an angle to the wall with which the strut is monolithically formed and in the expanded condition, the portion of the strut extends at a different angle to the wall with which the strut is monolithically formed; and
wherein the closed loop defines a width of the closed loop from one open side of the closed loop to the other open side and the width of the closed loop is greater in the expanded condition than in the compressed condition.

20. The intervertebral implant of claim 19, wherein the angle in the compressed condition is less than the different angle in the expanded condition.

* * * * *